United States Patent [19]
Abatjoglou et al.

[11] Patent Number: 5,929,289
[45] Date of Patent: Jul. 27, 1999

[54] STABILIZATION OF PHOSPHITE LIGANDS IN HYDROFORMYLATION PROCESS

[75] Inventors: Anthony George Abatjoglou, Charleston; David Robert Bryant, South Charleston; John Michael Maher, Charleston, all of W. Va.

[73] Assignee: Union Carbide Chemicals & Plastics Technology Corporation, Danbury, Conn.

[21] Appl. No.: 09/033,633

[22] Filed: Mar. 3, 1998

Related U.S. Application Data

[62] Division of application No. 08/293,028, Aug. 19, 1994, Pat. No. 5,756,855.

[51] Int. Cl.$^6$ .................. C07C 45/50; B01J 31/20
[52] U.S. Cl. .................. 568/454; 568/451; 502/158; 502/161; 502/166; 502/167
[58] Field of Search .................. 568/454, 451; 502/158, 161, 166, 167

[56] References Cited

U.S. PATENT DOCUMENTS

| | | | |
|---|---|---|---|
| 3,553,298 | 1/1971 | Hodan et al. | 260/967 |
| 3,597,461 | 8/1971 | L'Eplattenier et al. | 260/429 |
| 3,661,949 | 5/1972 | Fenton | 260/413 |
| 3,876,672 | 4/1975 | Mrowca | 260/410.9 R |
| 4,200,592 | 4/1980 | Hignett | 260/604 HF |
| 4,306,086 | 12/1981 | Demay | 568/454 |
| 4,453,019 | 6/1984 | Chang | 568/454 |
| 4,467,116 | 8/1984 | van Leeuwen et al. | 568/454 |
| 4,539,306 | 9/1985 | Chang | 502/154 |
| 4,567,306 | 1/1986 | Dennis | 568/455 |
| 4,599,206 | 7/1986 | Billig et al. | 558/85 |
| 4,599,323 | 7/1986 | Demay | 502/161 |
| 5,059,710 | 10/1991 | Abatjoglou | 558/78 |

FOREIGN PATENT DOCUMENTS

| | | |
|---|---|---|
| 0518241 | 6/1991 | European Pat. Off. . |
| 0590611 | 4/1994 | European Pat. Off. . |
| 348284 | 11/1956 | Switzerland . |

OTHER PUBLICATIONS

Anna M. Trzeciak et al., *Synthesis and Properties of the Orthometallated Rhodium Complex Rh{P(OPh)$_3$}$_3${P(OC$_6$H$_4$)(OPh)$_2$}* Z. anorg. allg. Chem. 577 (1989), pp. 255–262.

F.H. Westheimer, et al., *Rates and Mechanisms of Hydrolysis of Esters of Phosphorous Acid*, J. Am. Chem Soc. 1988, 110,pp. 181–185.

L.N. Lewis et al, *Catalytic C–C Bond Formation via Ortho–Metalated Complexes*, J. Am. Chem. Soc., vol. 108, No. 10, 1986, 1986, pp. 2728–2735.

*Primary Examiner*—Shailendra Kumar
*Assistant Examiner*—Sreeni Padmanabhan
*Attorney, Agent, or Firm*—Gerald L. Coon

[57] ABSTRACT

The present invention provides a hydroformylation process comprising: (1) forming a reaction mixture containing: (a) an olefinic compound, (b) hydrogen, (c) carbon monoxide, (d) a phosphite in which each phosphorus atom is bonded to three oxygen atoms and at least one such oxygen atom is bonded to a carbon atom of an aromatic ring that is adjacent to another carbon atom of said ring having a pendant monovalent group having a steric hindrance at least as great as the steric hindrance of the isopropyl group, (e) a catalytic amount of rhodium, and (f) a Group VIII metal (other than a rhodium) in an amount sufficient to reduce the rhodium-catalyzed decomposition of the phosphite during the hydroformylation process; and (2) maintaining the reaction mixture under conditions at which the olefinic compound reacts with the hydrogen and carbon monoxide to form an aldehyde.

2 Claims, No Drawings

STABILIZATION OF PHOSPHITE LIGANDS IN HYDROFORMYLATION PROCESS

This application is a divisional application of application Ser. No. 08/293,028 filed Aug. 19, 1994 now U.S. Pat. No. 5,756,855.

BACKGROUND OF THE INVENTION

1. Field of the Invention

The present invention relates to a process wherein certain metals are used in hydroformylation reaction mixtures containing phosphite ligands susceptible to rhodium-catalyzed degradation in order to stabilize the ligands against such degradation.

2. Description of Related Art

It is known to produce aldehydes by hydroformylating reaction mixtures comprising an olefinic compound, hydrogen, carbon monoxide, rhodium and a phosphite ligand. Complex catalysts formed in situ from the rhodium, ligand and carbon monoxide catalyze such hydroformylation reactions. Such processes are disclosed, for example in U.S. Pat. No. 4,599,206 which relates to the use of specific class of phosphite ligands (referred to therein as "diorganophosphite" ligands) in hydroformylation.

Such known hydroformylation processes suffer from the drawback that certain phosphite ligands are susceptible to rhodium-catalyzed decomposition which results not only in a loss of the expensive ligands but which may also result in deactivation of the rhodium by the ligand decomposition products. An example of one type of rhodium-catalyzed phosphite degradation is disclosed in "Synthesis and Properties of the Orthometallated Rhodium Complex Rh{P(OPh)$_3$}$_3${P(OC$_6$H$_4$)(OPh)$_2$}", Anna M. Trzeciak and Josef J. Ziolkowski, Z. Anorg. Allg. Chem. 577, (1989), 255–262.

Rhodium-catalyzed phosphite degradation is distinct from acid-catalyzed hydrolytic phosphite degradation disclosed, for example, in "Rates and Mechanisms of Hydrolysis of Esters of Phosphorous Acid", F. H. Westheimer, Shaw Huang, and Frank Covitz, J. Am. Chem. Soc., 1988, 110, 181–185. Phosphites sensitive to one of these forms of degradation may be relatively insensitive to the other form of degradation and stabilizers against one form of phosphite degradation do not necessarily stabilize against the other form of phosphite degradation. For example, published European Patent Application 0590611 discloses that epoxides stabilize phosphites against acid-catalyzed hydrolytic degradation in hydroformylation reaction mixtures but epoxides do not stabilize phosphites against rhodium-catalyzed degradation.

It is an object of the present invention to provide a hydroformylation process using phosphite ligands that are susceptible to, but are stabilized against, rhodium-catalyzed degradation.

Other objects of the present invention will be apparent from the description thereof appearing below.

SUMMARY OF THE INVENTION

The present invention provides hydroformylation process comprising: (1) forming a reaction mixture containing: (a) an olefinic compound, (b) hydrogen, (c) carbon monoxide, (d) a phosphite in which each phosphorus atom is bonded to three oxygen atoms and at least one such oxygen atom is bonded to a carbon atom of an aromatic ring that is adjacent to another carbon atom of said ring having a pendant monovalent group having a steric hindrance at least as great as the steric hindrance of the isopropyl group, (e) a catalytic amount of rhodium, and (f) a Group VIII metal (other than rhodium) in an amount sufficient to reduce the rhodium-catalyzed decomposition of the phosphite during the hydroformylation process; and (2) maintaining the reaction mixture under conditions at which the olefinic compound reacts with the hydrogen and carbon monoxide to form an aldehyde.

The present invention also provides a hydroformylation catalyst precursor composition comprising: (i) a rhodium catalyst precursor, (ii) a compound of a Group VIII metal (other than a rhodium compound) in an amount that provides a sufficient amount of the Group VIII metal to reduce the rhodium-catalyzed decomposition of the phosphite described in (iii) below during hydroformylation and (iii) a phosphite in which each phosphorus atom is bonded to three oxygen atoms and at least one such oxygen atom is bonded to a carbon atom of an aromatic ring that is adjacent to another carbon atom of said ring having a pendant monovalent group having a steric hindrance at least as great as the steric hindrance of the isopropyl group.

The present invention further provides a hydroformylation catalyst composition comprising: (i) rhodium in complex combination with carbon monoxide and a phosphite in which each phosphorus atom is bonded to three oxygen atoms and at least one such oxygen atom is bonded to a carbon atom of an aromatic ring that is adjacent to another carbon atom of said ring having a pendant monovalent group having a steric hindrance at least as great as the steric hindrance of the isopropyl group, and (ii) a Group VIII metal (other than a rhodium compound) in complex combination with carbon monoxide and said phosphite, said Group VIII metal being present in an amount sufficient to reduce the rhodium-catalyzed decomposition of the phosphite during hydroformylation.

DETAILED DESCRIPTION OF THE INVENTION

The reaction mixtures used in the process of the present invention contain rhodium. The rhodium functions as a hydroformylation catalyst in the form of a complex comprising the rhodium complexed with carbon monoxide and the phosphite ligand. When used herein to describe such complex catalysts, the term "comprising" is not meant to exclude, but rather includes, other ligands (e.g., hydrogen or other organic ligands, such as the olefin reactant) also complexed with the rhodium. However, the term "comprising" is meant to exclude materials in amounts which unduly poison or deactivate the catalyst. Thus, the catalyst is desirably free of significant amounts of contaminants such as rhodium-bound halogen (e.g., chlorine) and the like.

The complex catalysts involved in the process of the present invention may be formed by methods known in the art. For instance, preformed rhodium hydridocarbonyl (mono-phosphite) complexes may be prepared and introduced into the reaction mixture used in the hydroformylation process. Preferably, the catalysts used in this invention can be derived from a metal catalyst "precursor" which is introduced into the reaction mixture for in situ formation of the active catalyst complex in the reaction mixture. For example, rhodium catalyst precursors (such as rhodium dicarbonyl acetylacetonate, $Rh_2O_3$, $Rh_4(CO)_{12}$, $Rh_6(CO)_{16}$, $Rh(NO_3)_3$, rhodium acetylacetonate, and the like) may be introduced into the reaction mixture and the active catalyst complex can be formed in the reaction mixture by the precursor complexing with separately-added phosphite ligand and carbon monoxide. As a further example, in a preferred embodiment of the present invention, rhodium dicarbonyl acetylacetonate is reacted with a phosphite in presence of a solvent to form a rhodium carbonyl diorganophosphite acetylacetonate precursor. The precursor so formed is introduced into the hydroformylation reactor along with excess free phosphite ligand for the in situ formation of an active catalyst in the reactor by complexing with carbon monoxide in the reactor. In any event, it is sufficient for the purpose of this invention to understand that carbon monoxide and phosphites are ligands that are capable of being complexed with the rhodium (along with other ligands such as hydrogen and a portion of the olefin reactant) and that an active rhodium catalyst complex is present in the reaction mixture under the conditions of the hydroformylation process.

The phosphite ligands useful in the process of the present invention contain one or more trivalent phosphorus atoms and each valence of the phosphorus atom bonds the phosphorus atom to a carbon atom of an aromatic ring through an oxygen atom and that carbon atom of at least one of the aromatic rings is adjacent to another carbon atom of the aromatic ring to which is bonded a pendant monovalent group (hereinafter called "hindering group") having a steric hindrance at least as great as the steric hindrance of the isopropyl group. Illustrative of such blocking groups are branched alkyl groups containing at least 3 carbon atoms such as the isopropyl, secondary butyl, tertiary butyl, secondary amyl and tertiary amyl groups; cycloalkyl groups such as the cyclohexyl group; alkaryl groups such as the tolyl group; aralkyl groups such as the benzyl group and aryl groups such as the phenyl group. Phosphite ligands containing such hindering groups undergo rhodium-catalyzed degradation during hydroformylation in the absence of a Group VIII metal stabilizer. The Group VIII metal stabilizer reduces the decomposition of the phosphite by at least five percent by weight. For example, in the absence of a Group VIII metal stabilizer, at least about fifty weight percent of such phosphite ligands will decompose in rhodium-catalyzed hydroformylation process over a twelve day reaction period under the conditions used in Example 1 below. By way of comparison, under the conditions used in Example 1 below, less than about forty weight percent of such phosphite ligands will decompose in the presence of a Group VIII in accordance with the process of the present invention.

Suitable phosphite ligands useful in the process of the present invention include:

A. diorganophosphites having the formula:

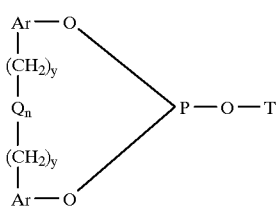

(I)

(1) Ar represents an aryl group, at least one of which aryl groups having a pendant hindering group ortho to the carbon atom to which the oxygen atom is attached;
(2) y has a value of 0 or 1;
(3) Q represents a divalent bridging group selected from the class consisting of —$CR^1R^2$—, —O—, —S—, —$NR_3$—, —$SiR^4R^5$—, and —CO—;
(4) $R^1$ and $R^2$ each represent a group selected from the group consisting of hydrogen, an alkyl group containing 1 to 12 carbon atoms and the phenyl, tolyl and anisyl groups;
(5) $R^3$, $R^4$, and $R^5$ each represent hydrogen or an alkyl group;
(6) n has a value of 0 to 1; and
(7) T represents a monovalent hydrocarbon group;

B. partially open ended bis-phosphites having the formula:

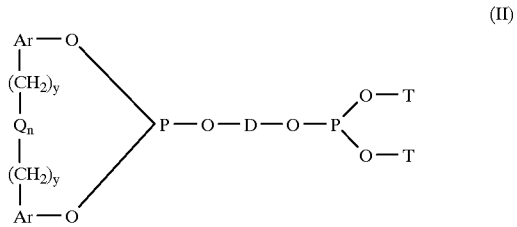

(II)

wherein D represents a divalent bridging group selected from the group consisting of alkylene, alkylene-oxy-alkylene, arylene, and arylene $(CH_2)_y$—$Q_n$—$(CH_2)_y$-arylene and wherein Ar, Q, n, y and T are as defined for formula (I) above;

C. triorganophosphites having the formula:

$(R^oO)_3P$ (III)

wherein $R^o$ is a substituted or unsubstituted monovalent aromatic group, at least one of which aromatic groups group has a pendant hindering group ortho to the carbon atom to which the oxygen atom is attached;

D. phosphites having the formula:

$P(OR^a)(OR^b)(OR^c)$ (IV)

wherein $R^a$, $R^b$ and $R^c$ each an represent aryl group, at least one of which aromatic groups group has a pendant hindering group ortho to the carbon atom to which the oxygen atom is attached, provided that at least one of $R^a$, $R^b$ and $R^c$ represents a group having the formula:

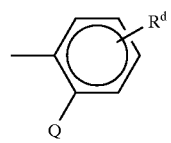

wherein Q represents a group having the formula:

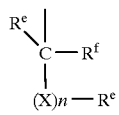

or a group having the formula:

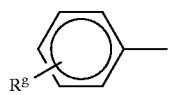

wherein each $R^e$ represents an optionally fluorine-containing hydrocarbyl group, $R^f$ represents a hydrogen atom or an $R^e$ group and $R^d$ represents a hydrogen atom or an inert (to the hydroformylation reaction) substituent on the meta and/or para position of the ring, X represents an oxygen or sulphur atom, n is 0 or 1 and $R^g$ represents a hydrogen atom or an inert (to the hydroformylation reaction) substituent of the ring;

E. polyphosphite ligands having the general formula:

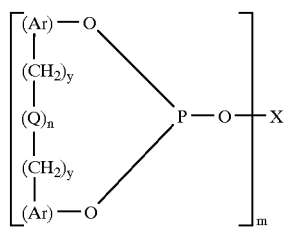

(V)

wherein each Ar group represents an identical or different aryl group, at least one of which aryl groups having a pendant hindering group ortho to the carbon atom to which the oxygen atom is attached; wherein X represents a m-valent radical selected from the group consisting of alkylene, alkylene-oxy-alkylene, arylene and arylene —$(CH_2)_y$—$(Q)_n$—$(CH_2)_y$-arylene, wherein each arylene radical is the same as Ar defined above; wherein each y individually has a value of 0 to 1; wherein each Q individually represents a divalent bridging group selected from the class consisting of —$CR^1R^2$—, —O—, —S—, —$NR^3$—, —$SiR^4R^5$— and —CO—, wherein each $R^1$ and $R^2$ radical individually represents a radical selected from the group consisting of hydrogen, alkyl of 1 to 12 carbon atoms, phenyl, tolyl and anisyl, wherein each $R^3$, $R^4$ and $R^5$ radical individually represents —H or —$CH_3$; wherein each n individually has a value of 0 to 1; and wherein m has a value of 2 to 6. Preferably each $R^1$ and $R^2$ individually represents —H or $CH_3$; and F. phosphite compounds having the formula:

$$A^1{\mathrm{-}}O{\mathrm{-}}P(OR^1)(OR^2)]_n \qquad (VI)$$

wherein $R^1$ and $R^2$ are aromatic groups which may be the same or different, at least one of which aromatic groups group has a pendants hindering group on a carbon atom adjacent to a carbon atom bonded to the oxygen atom; $A^1$ is an n-valent organic group having an aliphatic hydrocarbon group, a cycloaliphatic hydrocarbon group or an aromatic hydrocarbon group bonded with an adjacent oxygen atom, which may respectively have a substituent; n is an integer of from 2 to 4; and the respective

group may be the same or different.

Illustrative of the groups represented by the R groups in the above formulas (I) to (VI) above include aryl, alkaryl, aralkyl, alkyl, cycloalkyl, alkoxyaryl, hydroxyaryl, alkoxyalkyl, and hydroxyalkyl radicals. Representative R groups include phenyl, naphthyl, o-tolyl, 2-ethylphenyl, 2,6-dimethylphenyl, 4-t-butylphenyl, 4-iso-pentylphenyl, nonylphenyl, benzyl, 2-phenylethyl, 4-phenylbutyl, methyl, ethyl, n-propyl, iso-propyl, n-butyl, sec-butyl, t-octyl, n-decyl, iso-decyl, n-dodecyl, cyclohexyl, cyclopentyl, 4-methylcyclohexyl, p-methoxyphenyl, p-hydroxyphenyl, 2-ethoxyethyl, 2-hydroxyethyl, and the like.

In formulas (I) to (VI) above, the symbols can have the same or different meanings each time they occur (provided the meanings are within the above definitions).

Specific illustrative examples of the phosphite ligands employable in this invention within the scope of generic formulas (I) to (VI) above include such preferred ligands as:

Examples of generic formula (I):

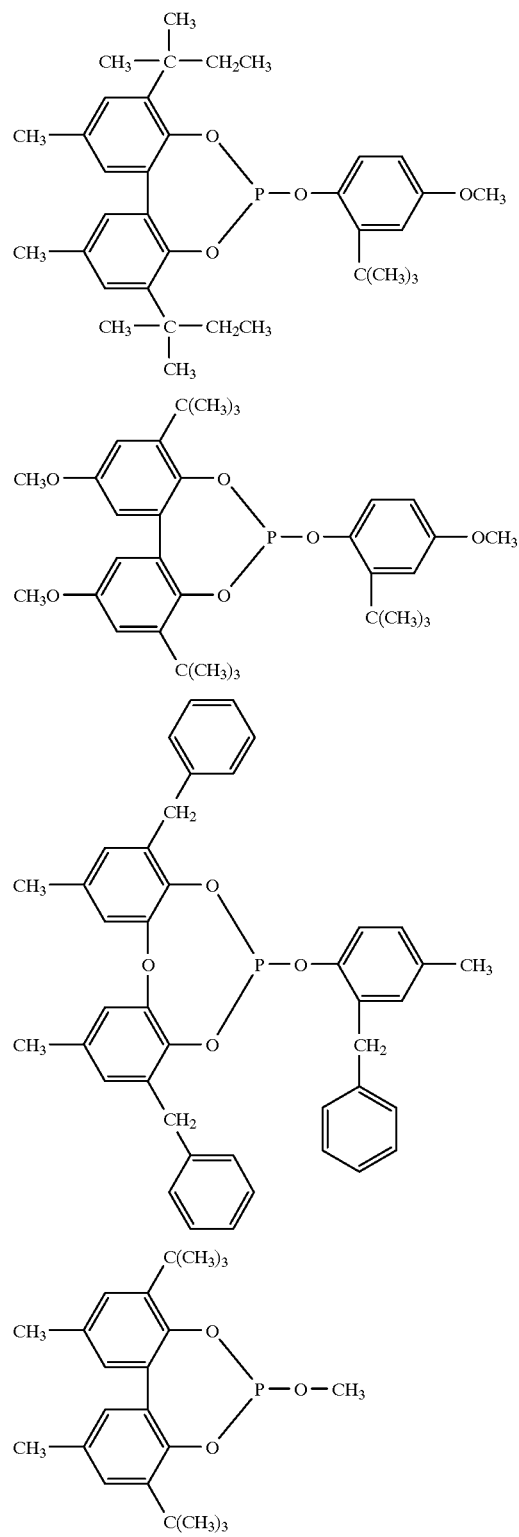

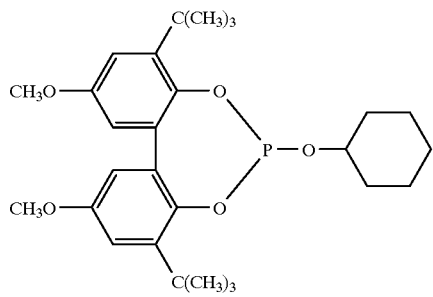
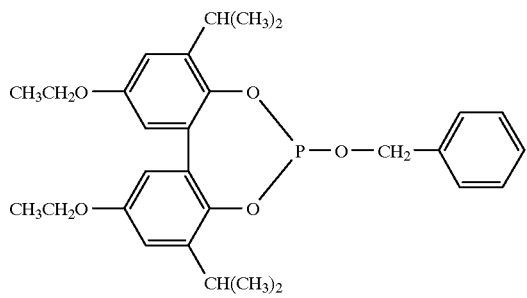
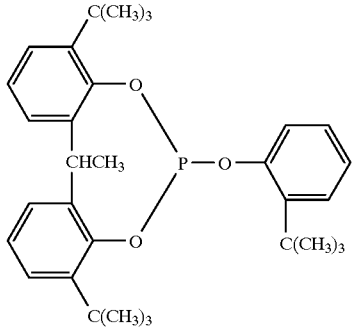
Examples of generic formula (II):
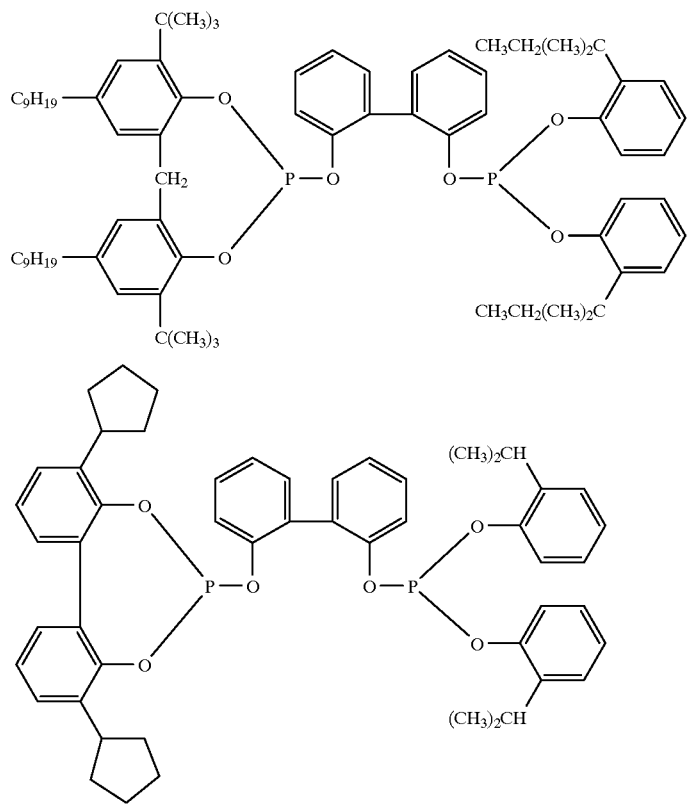

Examples of generic formulas (III) and (IV):
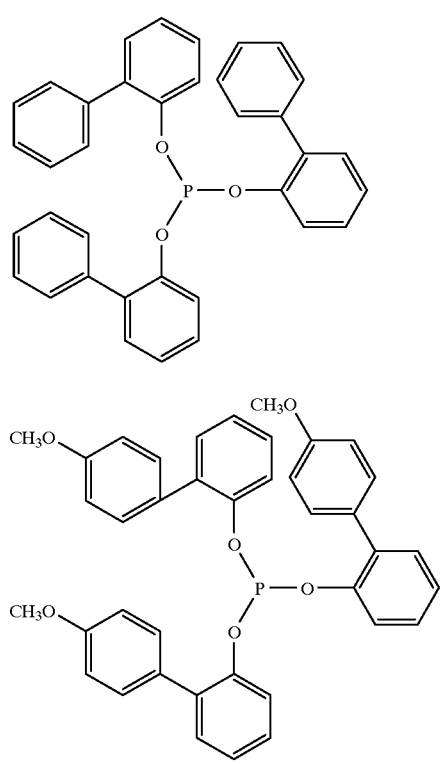
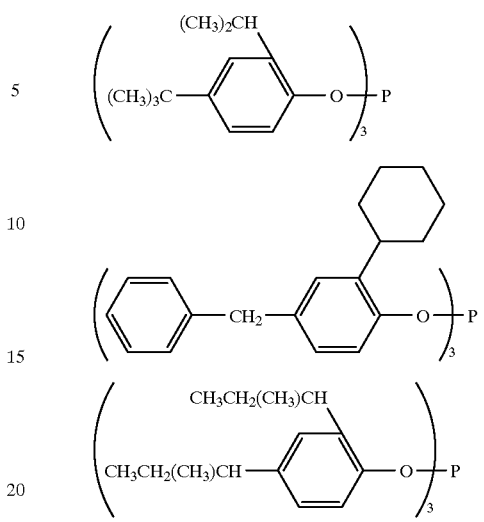
Examples of generic formula (V):
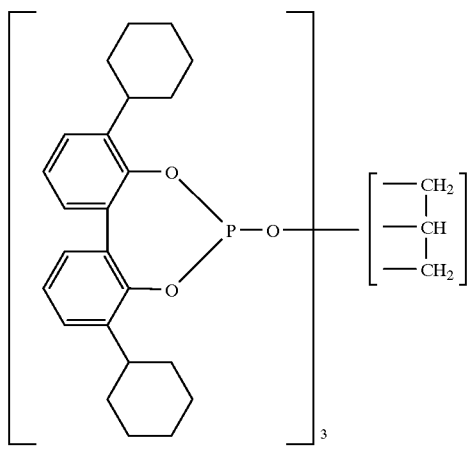

-continued
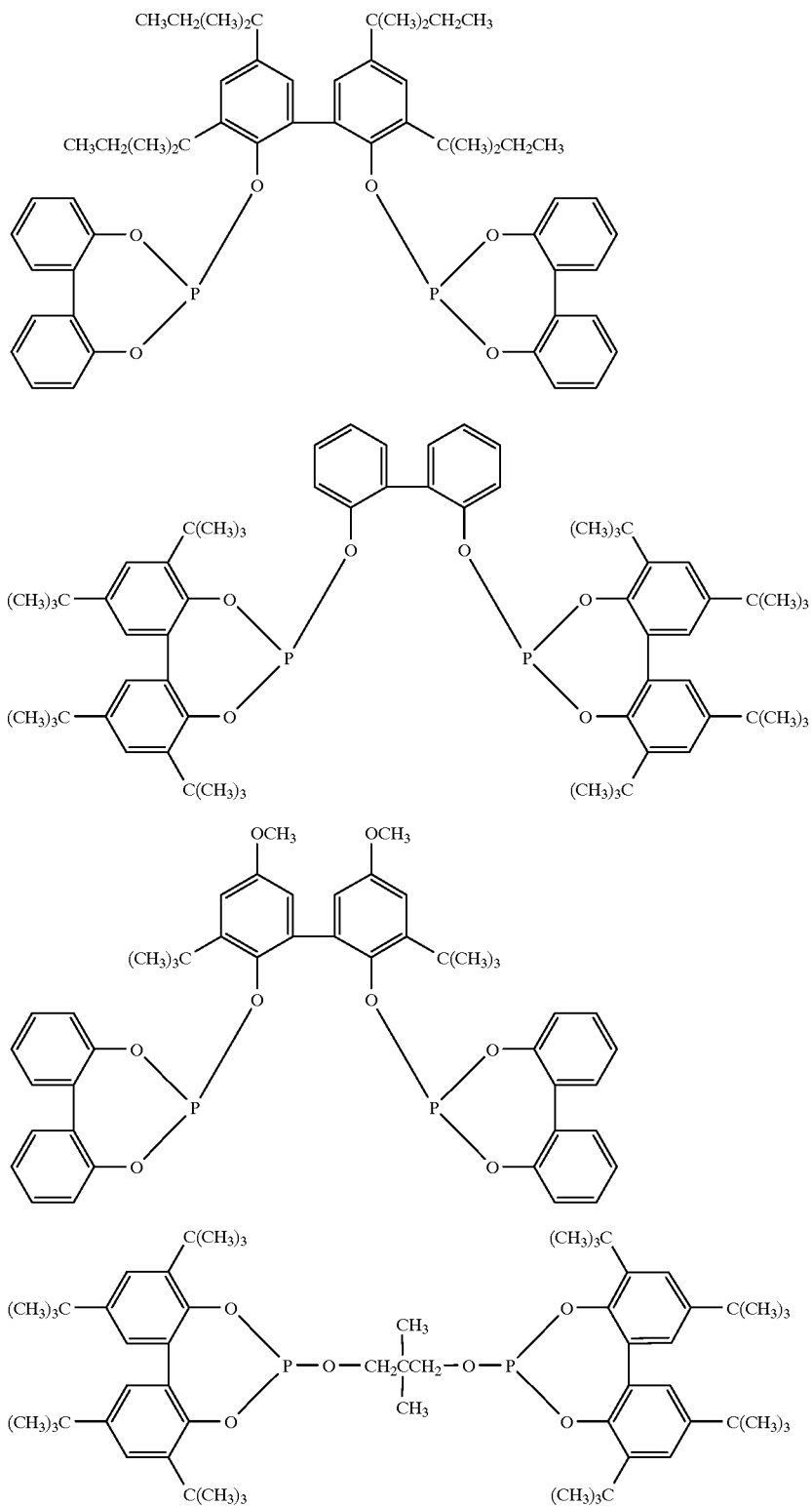

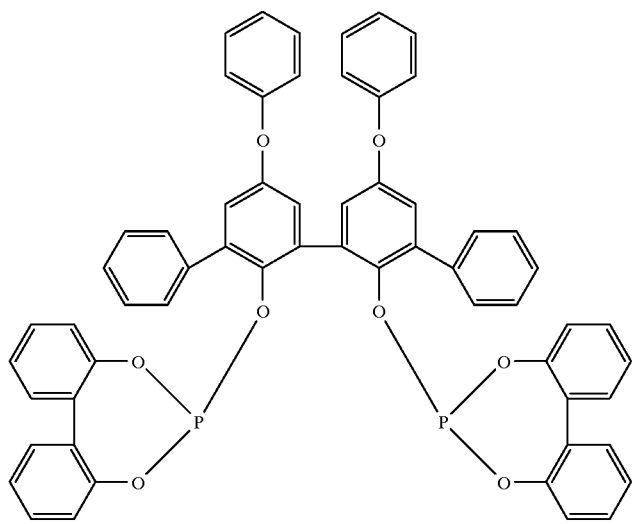
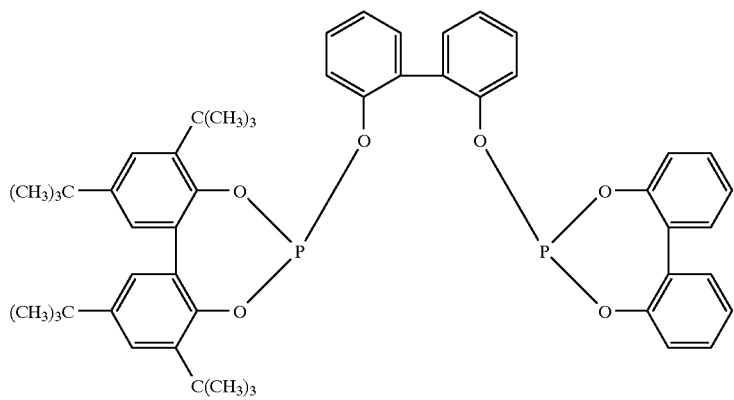
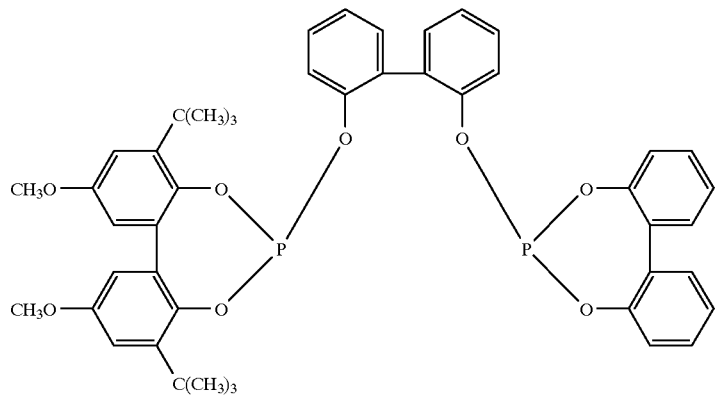

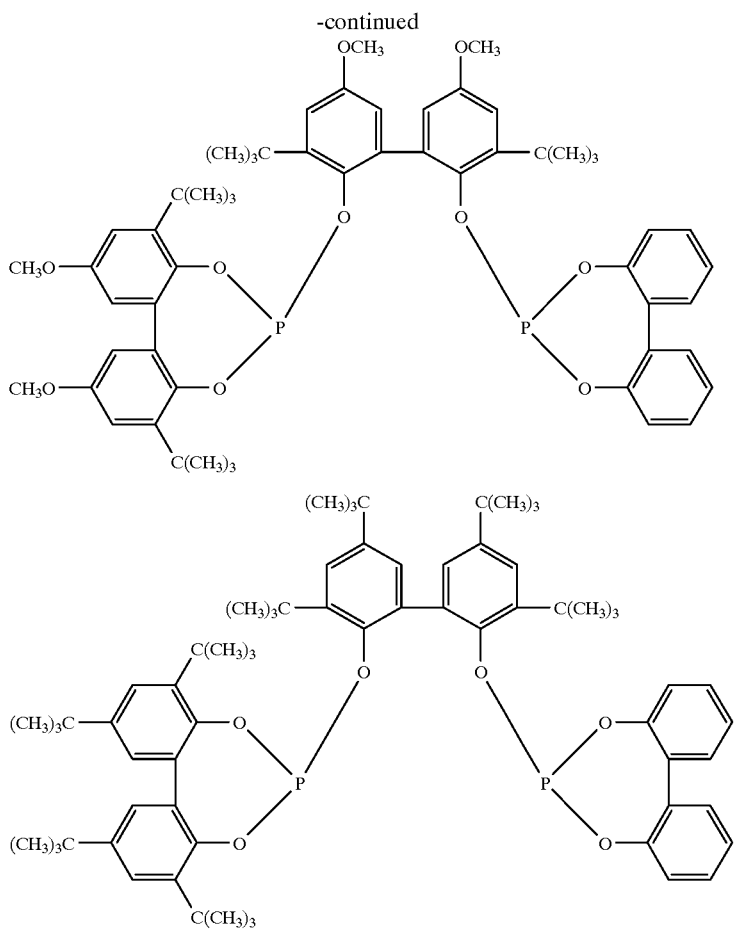
Examples of generic formula (VI):
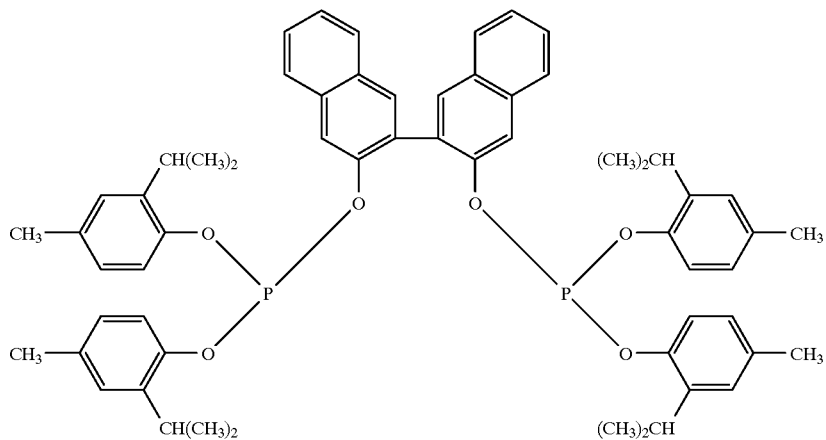

-continued

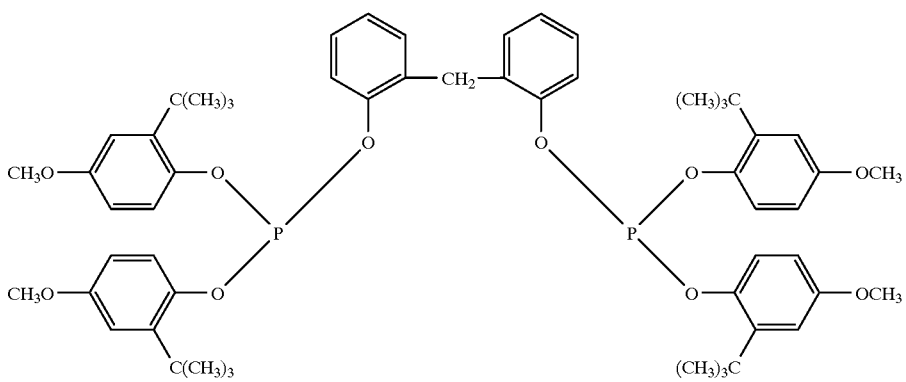

In the practice of the present invention, the Group VIII metal stabilizers are conveniently added to the hydroformylation in the form of stabilizer precursors. The Group VIII compounds used as phosphite stabilizer precursors in the process of the present invention include the Group VIII metal carbonyl acetylacetonates, oxides, acetylacetonates, carbonyls and nitrates. Preferred phosphite stabilizers are compounds of ruthenium, cobalt, palladium and platinum. In addition to containing the Group VIII metal, it is important that the stabilizer precursor compound is soluble in the hydroformylation reaction mixture and is free of rhodium catalyst poisons such as cyanides, halides and sulfur compounds. Rhodium compounds are useful as catalysts and/or catalyst precursors in the present invention, but are not useful as stabilizers. On the contrary, rhodium compounds catalyze degradation of the phosphites.

The amounts of the starting materials employed in the process of the present invention is not narrowly critical. Typically, the amount of the Group VIII compound used as a stabilizer precursor is the amount that provides up to a 10 molar excess of the Group VIII metal based on the rhodium in the hydroformylation reaction mixture. More usually, the amount of the Group VIII compound used as a stabilizer precursor is the amount that provides from 1 to 5 moles of the Group VIII metal per mole of rhodium in the hydroformylation reaction mixture. Typically, the amount of phosphite ligand in the hydroformylation reaction mixtures used in the process of the present invention is between about 0.005 and 15 weight percent based on the total weight of the reaction mixture. More usually, the ligand concentration is between 0.001 and 10 weight percent, and most often is between about 0.05 and 5 weight percent on that basis. Typically, the amount of rhodium in the hydroformylation reaction mixtures used in the process of the present invention is from 10 to 1000 parts per million by weight based on the weight of the reaction mixture, more typically the amount is between about 10 and 750 parts per million by weight based on the weight of the reaction mixture and most typically the amount is between about 20 and 500 parts per million by weight based on the total weight of the reaction mixture.

In the process of the present invention, the metal stabilizer precursor is added to and thoroughly mixed into the hydroformylation reaction mixture using any convenient procedure. The metal stabilizer precursor can be mixed with or dissolved in any of the reactants or solvent and added to the hydroformylation reaction mixture admixed with those materials or the precursor can be separately added to the reactant mixture. The metal stabilizer precursor can be added hydroformylation reaction mixture in small quantities over an extended period during the hydroformylation process. In this way, a concentration of metal stabilizer effective to stabilize the ligand during steady-state operation is maintained during the process. The metal stabilizer precursor also can be added initially to the hydroformylation reaction mixture at a higher than necessary concentration to achieve a long-term stabilization by allowing the concentration to fall to lower, but still effective, concentrations during the process without further addition of stabilizer. The stabilizer precursor is converted in the hydroformylation reaction mixture to an active complex comprising the stabilizing metal in complex combination with carbon monoxide and the above-described phosphite ligands. The complex may also contain other ligands (e.g., the hydrogen and the olefin reactant).

The hydroformylation reaction conditions that may be employed in the process of the present invention generally include the conditions heretofore disclosed in the art for hydroformylation using catalysts comprising rhodium and phosphite ligands. For instance, the total gas pressure of hydrogen carbon monoxide and olefinic unsaturated starting compound of the hydroformylation process may range from about 1 to about 10,000 psia (pound per square inch absolute). In general, however, it is preferred that the process be operated at a total gas pressure of hydrogen, carbon monoxide and olefinic compound of less that about 1500 psia and more preferably less than about 500 psia. The minimum total pressure being limited predominately by the amount of reactants necessary to obtain a desired rate of reaction. More specifically, the carbon monoxide partial pressure is preferably from about 1 to about 120 psia and, more preferably, from about 3 to about 90 psia, while the hydrogen partial pressure is preferably about 15 to about 160 psia and, more preferably, from about 30 to about 100 psia. In general $H_2:CO$ molar ratio of gaseous hydrogen to carbon monoxide may range from about 1:10 to 100:1 or higher, the more preferred hydrogen to carbon monoxide molar ratio being from about 1:1 to about 10:1. Further, the hydroformylation process may be conducted at a reaction temperature from about 45° C. to about 150°. In general, hydroformylation reaction temperature of about 50° C. to about 120° are preferred for all types of olefinic starting materials. The more preferred reaction temperatures are from about 50° C. to about 100° C.

The olefinic compounds used as starting materials in the hydroformylation process of the present invention include olefinic compounds containing from 2 to 30 carbon atoms. Such olefinic compounds can be terminally or internally unsaturated and be of straight-chain, branched chain or cyclic structures such as obtained from the oligomerization of propene, butene and isobutene as well as dimeric, trimeric or tetrameric propylene and the like disclosed in U.S. Pat. Nos. 4,518,809 and 4,528,403. Moreover, mixtures of two or more different olefinic compounds may be employed as the starting hydroformylation material if desired. Further, such olefinic compounds and the corresponding aldehyde products derived therefrom may also contain one or more groups or substituents which do not unduly adversely affect the hydroformylation process or the process of this invention such as described, e.g., in U.S. Pat. Nos. 3,527,809 and 4,668,651.

Illustrative olefinic compounds are alpha-olefins, internal olefins, alkyl alkenoates, alkenyl alkanoates, alkenyl alkyl ethers, alkenols, and the like, e.g., ethylene, propylene, 1-butene, 1-pentene, 1-hexene, 1-octene, 1-nonene, 1-decene, 1-undecene, 1-dodecene, 1-tridecene, 1-tetradecene, 1-pentadecene, 1-hexadecene,1-heptadecene, 1-octadecene, 1-nonadecene, 1-eicosene, 2-butene, 2-methyl propene (isobutylene), 2-methylbutene, 2-pentene, 2-hexene, 3-hexane, 2-heptene, cyclohexene, propylene dimers, propylene trimers, propylene tetramers, 2-ethyl-1-hexene, 2-octene, styrene, 3-phenyl-1-propene, 3-cyclohexyl-1-butene, allyl alcohol, allyl butyrate, hex-1-en-4-ol, oct-1-en-4-ol, vinyl acetate, allyl acetate, 3-butenyl acetate, vinyl propionate, allyl propionate, methyl methacrylate, vinyl ethyl ether, vinyl methyl ether, allyl ethyl ether, methyl-3-pentenoate, n-propyl-7-octenoate, 3-butenenitrile, 5-hexenamide, 4-methyl styrene, 4-isopropyl styrene, 4-tert-butyl styrene, alpha-methyl styrene, 4-tert-butyl-alpha-methyl styrene, 1,3-diisopropenyl-benzene, eugenol, iso-eugenol, safrole, iso-safrole, anethol, 4-allylanisole, indene, limonene, beta-pinene and the like.

Mixtures of different olefinic compounds can be used as starting materials in the hydroformylation process of the present invention. The present invention is especially useful for the production of aldehydes by hydroformylating alpha mono-olefinic hydrocarbons containing from 2 to 20 carbon atoms and internal olefinic hydrocarbons containing from 4 to 20 carbon atoms as well as mixtures of such alpha-olefins and internal olefins. Commercial-alpha-mono-olefins containing four or more carbon atoms may contain minor amounts of corresponding internal mono-olefins and/or their corresponding saturated hydrocarbon and that such commercial mono olefins need not necessarily be purified from same prior to being hydroformylated.

The hydroformylation process of the present invention can be conducted in the presence of an organic solvent for the rhodium-phosphite catalyst and any free phosphite ligand that might be present. Any suitable solvent which does not unduly adversely interfere with the intended hydroformylation reaction can be employed. Suitable solvents for rhodium-catalyzed hydroformylation processes include those disclosed in U.S. Pat. No. 4,668,651 and also include saturated hydrocarbons, aromatic hydrocarbons, ethers, aldehydes, ketones, nitriles and aldehyde condensation products. Illustrative solvents include tetraglyme, pentanes, cyclohexane, benzene, xylene, toluene, diethyl ether, butyraldehyde, valeraldehyde, acetophenone, cyclohexanone, benzonitrile and Texanol® (2,4,4,-trimethyl-1,3-pentanediol monoisobutyrate sold by Eastman Kodak Company). Mixtures of one or more different solvents may be employed if desired. Most preferably, the solvent is a liquid organic compound in which the olefinic starting material, catalyst and ligand are all substantially soluble. In general, it is preferred to employ aldehyde compounds corresponding to the aldehyde products desired to be produced and/or higher boiling aldehyde liquid condensation by-products as the primary solvent, such as the higher boiling aldehyde liquid condensation by-products that are produced in situ during the hydroformylation process. Indeed, while one may employ any suitable solvent at the start up of a continuous process, the primary solvent in such a process will normally eventually comprise both aldehyde products and higher boiling aldehyde liquid condensation by-products due to the nature of such continuous processes. Such aldehyde condensation by-products can also be preformed and used from the start of the process. The amount of solvent employed is not critical to the present invention and need only be that amount sufficient to provide the reaction medium with the particular rhodium concentration desired for a given process. In general, the amount of solvent may range from about 5 percent by weight up to about 95 percent by weight or more based on the total weight of the reaction mixture.

The hydroformylation process of this invention can be conducted using any suitable procedure, e.g., the liquid recycle procedure. Such liquid catalyst recycle procedures are known as seen disclosed, e.g., in U.S. Pat. Nos. 4,668,651; 4,774,361; 5,102,505 and 5,110,990. For instance, in such liquid catalyst recycle procedures, it is commonplace to continuously remove a portion of the liquid reaction product medium, containing, e.g., the aldehyde product, the solubilized rhodium-phosphite catalyst, free phosphite ligand and organic solvent, as well as by-products produced in situ by the hydroformylation (e.g., aldehyde condensation by-products etc.) and unreacted mono-olefinic starting material, carbon monoxide and hydrogen (syn gas) dissolved in said medium from the hydroformylation reactor, to a distillation zone (e.g., a vaporizer/separator) wherein the desired aldehyde product is distilled in one or more stages under normal, reduced or elevated pressure, as appropriate, and separated from the liquid medium. The vaporized or distilled desired aldehyde product so separated may then be condensed and recovered in any conventional manner. The remaining non-volatilized liquid residue which contains rhodium-phosphite complex catalyst, solvent, free phosphite ligand and usually some undistilled aldehyde product is then recycled back, with or without further treatment as desired, along with whatever by-product and non-volatilized gaseous reactants that might still also be dissolved in said recycled liquid residue, in any conventional manner desired, to the hydroformylation reactor. Moreover, the reactant gases so removed by such distillation from the vaporizer may also be recycled back to the reactor if desired.

After the hydroformylation process of the present invention is conducted, separation of the desired aldehyde product from the crude reaction product may take place in any suitable manner. Separation is usually accomplished by distillation at relatively low temperatures, such as below 150° C., and more preferably at a temperature in the range of from about 50° C. to about 130° C. It is also preferred that such aldehyde distillation take place under reduced pressure e.g., a total gas pressure that is substantially lower than the total gas pressure employed during hydroformylation when low boiling aldehydes (e.g., $C_4$ to $C_6$ aldehydes) are involved or under vacuum when high boiling aldehydes (e.g., $C_7$ aldehydes or higher aldehydes) are involved. For instance, the crude reaction product of the hydroformylation process is subjected to a pressure reduction so as to volatilize a substantial portion of the unreacted gases dissolved in the product, the liquid product (which now contains a much lower synthesis gas concentration than was present in the crude reaction product) to the distillation zone where the desired aldehyde product is distilled. In general, distillation pressures ranging from vacuum pressures or below on up to total gas pressure of about 50 psig should be sufficient for most purposes.

Infrared examination of a crude hydroformylation reaction product containing phosphite-modified rhodium catalyst which does not contain another Group VIII metal (such as a ruthenium compound) as a phosphite stabilizer shows that some of the rhodium catalyst has formed the rhodium cluster having a formula: $Rh_6(CO)_{16}$. When ruthenium has been used as a stabilizer, either no $Rh_6(CO)_{16}$ is seen, or the quantities of that cluster are reduced. Without wishing to be bound by any particular theory, it is believed and that either $Rh_6(CO)_{16}$ or other rhodium aggregate complexes which exist with $Rh_6(CO)_{16}$ (or intermediates leading to such complexes) are responsible for catalyzing the decomposition of phosphite ligands and that ruthenium (or other Group VIII metal) reduces the concentration of these complexes present in the hydroformylation reaction mixture. In any event, it has been found that by reducing the concentrations of these rhodium aggregates through addition of Group VIII metal such as ruthenium, the extent of rhodium-catalyzed degradation of the phosphite ligand is reduced.

In addition to reducing the degradation of phosphites as described above, some Group VIII metals (particularly ruthenium, platinum, cobalt and osmium) also reduce the extent of undesired precipitation of rhodium from rhodium/phosphite-catalyzed hydroformylation reaction mixtures (see Examples 9 to 14 below). Such precipitation of rhodium decreases the amount of active rhodium hydroformylation catalyst.

In the Examples appearing below, the abbreviations used have the following meanings:

| | |
|---|---|
| mL | milliliters |
| ° C. | degrees centigrade |
| ppmw or ppm | parts per million by weight |
| wt. % | weight percent |
| g mol/L/hr | gram moles per liter per hour |
| N/I | moles of normal butyraldehyde per mole of isobutyraldehyde in the reaction product |
| Ligand I | Formula and name given below |
| Ligand II | Formula and name given below |
| acac | acetylacetonate |

The following Examples illustrate the present invention.

EXAMPLES 1 TO 8

Eight experiments (Examples 1 to 8) were conducted involving the hydroformylation of propylene with hydrogen and carbon monoxide using rhodium carbonyl acetylacetonate as the catalyst precursor, "Ligand I" or "Ligand II" as the phosphite ligand and tetraglyme as the solvent. The formula and name of Ligands I and II are as follows:

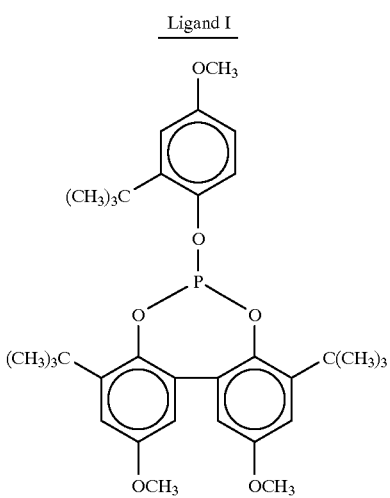

Ligand I 4,8-bis(1,1-dimethylethyl)-6-[2-(1,1-dimethylethyl)-4-methoxyphenoxy]-2,10-dimethoxydibenzo[d,f][1,3,2]dioxaphosphepin

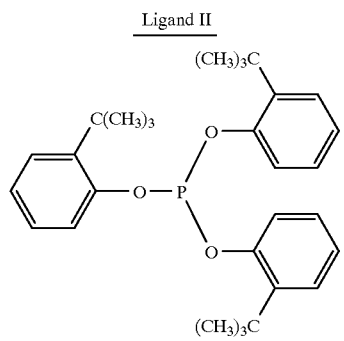

Ligand II tris-ortho-tert-butylphenyl phosphite

The experiments were conducted with and without a transition metal stabilizer and the composition of the reaction mixtures used in the experiments are shown in Table 1. The experiments were conducted as follows:

The hydroformylation reactions were conducted in a glass pressure reactor operating in a continuous mode. The reactor consisted of a three-ounce pressure bottle partially submersed in an oil bath with a glass front for viewing. After purging the system with nitrogen, about 20-mL of a freshly prepared rhodium catalyst precursor solution was charged to the reactor with a syringe. The catalyst precursor solution contained about 250 ppm rhodium (introduced as rhodium dicarbonyl acetylacetonate), metal stabilizer precursor (where used), ligand and tetraglyme as solvent. After sealing the reactor, the system was again purged with nitrogen, and the oil bath was heated to furnish the desired hydroformylation reaction temperature. The hydroformylation reaction was conducted at a total gas pressure of about 160 psig and 100° C. reaction temperature. The partial pressures of hydrogen, carbon monoxide, and propylene during the reaction are given in Tables 2 to 7 below. The remainder of the pressure of the reaction mixture is from the partial pressures of nitrogen and aldehyde product. The flows of the feed gases (carbon monoxide, hydrogen, propylene and nitrogen)

were controlled individually with mass flow meters and the feed gases were dispersed in the catalyst precursor solution via fritted metal spargers. The unreacted portion of the feed gases was stripped out the butyraldehydes produced in the reaction. The outlet gas was analyzed over the indicated number of days of continuous operation. The analytical results for Examples 1 to 6 are given in Tables 2 to 7 below. The average reaction rates for Examples 1 to 6 (in terms of gram moles per liter per hour of the butyraldehyde products) as well as the n-butyraldehyde to iso-butyraldehyde product ratio (N/I) for those Examples that are also given in Tables 2 to 7 below.

TABLE 1

Composition of Reaction Mixtures Used in Examples 1–8 to Determine the Effect of Added Metal Stabilizers on Ligand Stabilization.

| Example | Tetraglyme grams | Ligands I grams | $Rh(CO)_2acac$ Catalyst grams | Dodecaphenone *** grams | Stabilizer/ Grams |
|---|---|---|---|---|---|
| 1. | 29.5 | 0.405* | 0.0189 | 0.30 | None |
| 2. | 29.5 | 0.405* | 0.0191 | 0.30 | $Ru_3(CO)_{12}$/ 0.0316 |
| 3. | 29.5 | 0.405* | 0.0189 | 0.30 | $Co_2(CO)_8$/ 0.0249 |
| 4. | 29.5 | 0.405* | 0.019 | 0.30 | $Pt(acac)_2$/ 0.0573 |
| 5. | 29.5 | 0.405* | 0.0189 | 0.30 | $Pd(acac)_2$/ 0.0448 |
| 6. | 29.5 | 0.405* | 0.0188 | 0.30 | $Os_3(CO)_{12}$/ 0.0442 |
| 7. | 28.2 | 1.2** | 0.0152 | 0.30 | None |
| 8. | 28.2 | 1.2** | 0.0152 | 0.30 | $Co_2(CO)_8$/ 0.0199 |

*Ligand I was used in the experiment
**Ligand II was used in the experiment
***Internal standard for liquid chromatography.

TABLE 2

Example 1. Control. Ligand I, no Stabilizer
Reaction Rate Test Results - Daily Averages

| | Partial Pressure psi | | | Rate | N/I |
|---|---|---|---|---|---|
| Days | CO | H2 | C3H6 | gmol/L/hr | Ratio |
| 0.6 | 53.1 | 46.4 | 13.3 | 2.050 | 0.8 |
| 1.5 | 51.3 | 47.4 | 16.5 | 1.732 | 0.7 |
| 2.5 | 51.9 | 46.8 | 16.9 | 1.530 | 0.7 |
| 3.6 | 52.1 | 46.8 | 17.1 | 1.458 | 0.7 |
| 4.5 | 52.4 | 46.8 | 17.2 | 1.508 | 0.8 |
| 5.5 | 52.5 | 47.1 | 17.7 | 1.427 | 0.8 |
| 6.5 | 52.2 | 47.0 | 18.0 | 1.471 | 0.8 |
| 7.5 | 51.6 | 46.7 | 18.0 | 1.433 | 0.8 |
| 8.4 | 51.3 | 46.6 | 18.5 | 1.462 | 0.8 |
| 9.4 | 50.9 | 46.3 | 18.7 | 1.491 | 0.8 |
| 10.1 | 50.8 | 46.5 | 18.3 | 1.454 | 0.7 |
| 11.1 | 50.6 | 46.1 | 19.1 | 1.370 | 0.7 |
| 12.4 | 50.5 | 46.1 | 19.7 | 1.428 | 0.8 |
| 13.5 | 51.9 | 45.2 | 20.0 | 1.422 | 0.8 |
| 14.5 | 52.4 | 45.0 | 20.6 | 1.409 | 0.8 |

TABLE 3

Example 2. Ligand I, Ruthenium Stabilizer
Reaction Rate Test Results - Daily Averages

| | Partial Pressure psi | | | Rate | N/I |
|---|---|---|---|---|---|
| Days | CO | H2 | C3H6 | gmol/L/hr | Ratio |
| 0.5 | 51.4 | 47.2 | 21.9 | 1.376 | 0.8 |
| 1.5 | 49.0 | 46.0 | 27.0 | 1.063 | 0.7 |
| 2.4 | 48.6 | 45.1 | 31.2 | 1.011 | 0.7 |
| 3.5 | 48.5 | 45.0 | 32.2 | 0.954 | 0.7 |
| 4.5 | 48.3 | 45.0 | 32.9 | 0.950 | 0.7 |
| 5.4 | 48.7 | 45.0 | 33.4 | 0.948 | 0.7 |
| 6.5 | 49.3 | 45.6 | 32.3 | 0.976 | 0.7 |
| 7.5 | 49.5 | 44.5 | 32.8 | 1.024 | 0.7 |
| 8.4 | 49.9 | 45.0 | 31.6 | 1.014 | 0.7 |
| 9.4 | 49.3 | 44.6 | 34.8 | 1.039 | 0.7 |
| 10.1 | 49.2 | 44.1 | 35.0 | 1.085 | 0.7 |
| 11.1 | 49.2 | 44.2 | 35.1 | 1.129 | 0.7 |
| 12.4 | 48.9 | 44.5 | 35.5 | 1.103 | 0.7 |
| 13.5 | 49.3 | 45.2 | 35.3 | 1.163 | 0.7 |
| 14.5 | 49.7 | 45.6 | 35.1 | 1.179 | 0.7 |

TABLE 4

Example 3. Ligand I, Cobalt Stabilizer
Reaction Rate Test Results - Daily Averages

| | Partial Pressure psi | | | Rate | N/I |
|---|---|---|---|---|---|
| Days | CO | H2 | C3H6 | gmol/L/hr | Ratio |
| 0.5 | 50.7 | 50.0 | 25.3 | 0.321 | 0.9 |
| 1.4 | 49.4 | 47.4 | 26.1 | 0.616 | 0.8 |
| 2.5 | 47.5 | 46.5 | 26.2 | 0.831 | 0.8 |
| 3.2 | 46.9 | 46.2 | 26.4 | 0.888 | 0.8 |
| 4.2 | 47.1 | 46.1 | 26.4 | 0.929 | 0.9 |
| 5.5 | 47.3 | 45.6 | 26.4 | 0.915 | 1.0 |
| 6.6 | 47.8 | 44.9 | 26.7 | 0.933 | 1.0 |
| 7.6 | 48.1 | 44.8 | 26.7 | 0.950 | 1.0 |
| 8.6 | 48.0 | 44.8 | 26.5 | 0.957 | 0.9 |
| 9.5 | 48.0 | 44.9 | 26.8 | 1.060 | 0.9 |
| 10.6 | 48.1 | 44.7 | 26.6 | 1.134 | 0.9 |
| 11.6 | 47.4 | 44.4 | 26.0 | 1.231 | 0.8 |
| 12.6 | 47.4 | 44.5 | 25.7 | 1.358 | 0.8 |
| 13.6 | 47.3 | 44.7 | 25.3 | 1.472 | 0.8 |

TABLE 5

Example 4. Ligand I, Platinum Stabilizer
Reaction Rate Test Results - Daily Averages

| | Partial Pressure psi | | | Rate | N/I |
|---|---|---|---|---|---|
| Days | CO | H2 | C3H6 | gmol/L/hr | Ratio |
| 0.5 | 51.1 | 47.5 | 9.8 | 1.275 | 0.8 |
| 1.4 | 52.1 | 48.3 | 12.4 | 0.999 | 0.8 |
| 2.5 | 52.1 | 48.5 | 13.7 | 0.922 | 0.8 |
| 3.2 | 52.0 | 48.0 | 14.0 | 0.944 | 0.8 |
| 4.2 | 49.7 | 46.6 | 13.7 | 0.865 | 0.8 |
| 5.5 | 51.1 | 48.2 | 14.3 | 0.871 | 0.8 |
| 6.6 | 52.8 | 47.4 | 15.2 | 0.847 | 0.8 |
| 7.6 | 53.1 | 47.0 | 15.8 | 0.846 | 0.8 |
| 8.6 | 53.3 | 46.3 | 15.8 | 0.846 | 0.8 |
| 9.6 | 52.5 | 46.3 | 17.7 | 0.959 | 0.8 |
| 10.6 | 52.3 | 46.4 | 18.0 | 0.927 | 0.8 |
| 11.6 | 52.2 | 46.5 | 18.0 | 0.912 | 0.8 |
| 12.6 | 51.6 | 46.4 | 18.5 | 0.918 | 0.8 |
| 13.6 | 51.6 | 46.0 | 19.2 | 0.955 | 0.8 |

TABLE 6

Example 5. Ligand I, Palladium Stabilizer
Reaction Rate Test Results - Daily Averages

| Days | Partial Pressure psi | | | Rate | N/I |
|---|---|---|---|---|---|
| | CO | H2 | C3H6 | gmol/L/hr | Ratio |
| 0.5 | 51.5 | 47.2 | 10.1 | 1.246 | 0.7 |
| 1.4 | 51.5 | 46.1 | 11.2 | 1.188 | 0.8 |
| 2.5 | 51.5 | 45.6 | 12.4 | 1.175 | 0.8 |
| 3.2 | 51.4 | 45.7 | 12.5 | 1.198 | 0.8 |
| 4.2 | 51.2 | 45.6 | 12.7 | 1.280 | 0.8 |
| 5.5 | 51.2 | 45.2 | 13.2 | 1.233 | 0.8 |
| 6.6 | 51.4 | 45.2 | 14.0 | 1.213 | 0.8 |
| 7.6 | 51.8 | 45.3 | 14.3 | 1.218 | 0.8 |
| 8.5 | 51.5 | 44.5 | 14.4 | 1.203 | 0.8 |
| 9.6 | 52.1 | 44.4 | 15.0 | 1.230 | 0.8 |
| 10.6 | 52.5 | 44.4 | 15.3 | 1.181 | 0.8 |
| 11.6 | 52.3 | 44.7 | 15.2 | 1.146 | 0.8 |
| 12.5 | 51.1 | 45.2 | 15.2 | 1.166 | 0.8 |
| 13.6 | 51.1 | 44.3 | 15.8 | 1.175 | 0.8 |

TABLE 7

Example 6. Ligand I, Osmium Stabilizer
Reaction Rate Test Results - Daily Averages

| Days | Partial Pressure psi | | | Rate | N/I |
|---|---|---|---|---|---|
| | CO | H2 | C3H6 | gmol/L/hr | Ratio |
| 0.5 | 51.0 | 47.1 | 10.1 | 1.275 | 1.0 |
| 1.4 | 51.2 | 46.7 | 10.6 | 1.449 | 0.8 |
| 2.5 | 50.9 | 46.8 | 11.2 | 1.369 | 0.8 |
| 3.2 | 50.8 | 46.5 | 11.4 | 1.379 | 0.8 |
| 4.2 | 50.5 | 46.3 | 11.6 | 1.410 | 0.8 |
| 5.5 | 50.6 | 46.8 | 12.4 | 1.395 | 0.8 |
| 6.6 | 51.7 | 46.0 | 13.1 | 1.337 | 0.8 |
| 7.6 | 52.2 | 46.0 | 13.7 | 1.283 | 0.8 |
| 8.6 | 52.3 | 45.9 | 14.5 | 1.240 | 0.8 |
| 9.5 | 51.7 | 45.6 | 15.6 | 1.260 | 0.8 |
| 10.6 | 51.9 | 46.1 | 16.0 | 1.204 | 0.8 |
| 11.5 | 51.5 | 46.2 | 16.0 | 1.181 | 0.8 |
| 12.5 | 51.5 | 46.0 | 17.3 | 1.182 | 0.8 |
| 13.5 | 51.5 | 46.0 | 17.3 | 1.182 | 0.8 |

The Ligand I concentrations in the hydroformylation reaction mixtures during Examples 1–6 was monitored by High Performance Liquid Chromatography of catalyst samples removed from each reactor periodically. The results of these analyses are presented below in Tables 8, 9, 10. The data in Table 8 (presented as percent Ligand I remaining with time) show that one half of the Ligand I in the control experiment (no added metal stabilizer) decomposed in 12 to 15 days of continuous hydroformylation whereas similar reaction mixtures containing cobalt or platinum as stabilizers show very little Ligand I decomposition.

TABLE 8

Ligand I Decomposition Rates in the Presence and Absence of Transition Metal Stabilizers: Comparative Experiments with and without added Cobalt or Platinum.

| Days of Operation | Example 1 Rh/Ligand I (Control) | Example 3 Rh/Co/Ligand I | Example 4 Rh/Pt/Ligand I |
|---|---|---|---|
| | Percent Ligand I Remaining | | |
| 1 | 100 | 100 | 100 |
| 5 | 72 | 104 | 92 |
| 8 | 66 | 97 | 96 |
| 12 | 53 | 103 | 94 |
| 15 | 49 | — | — |

Similarly, ruthenium and palladium were also found to stabilize Ligand I (see Table 9 below).

TABLE 9

Ligand I Decomposition Rates in the Presence and Absence of Transition Metal Stabilizers: Comparative Experiments with and without added Palladium or Ruthenium.

| Days of Operation | Example 1 Rh/Ligand I (Control) | Example 5 Rh/Pd/Ligand I | Example 2 Rh/Ru/Ligand I |
|---|---|---|---|
| | Percent Ligand I Remaining | | |
| 1 | 100 | 100 | 96 |
| 5 | 72 | 87 | 75 |
| 8 | 66 | 82 | 73 |
| 12 | 53 | 78 | 67 |
| 15 | 49 | — | 64 |

Unlike the other metals tested above, osmium showed very small stabilizing effect (Table 10).

TABLE 10

Ligand I Decomposition Rates in the Presence and Absence of Transition Metal Stabilizers: Comparative Experiments with and without added Osmium

| Days of Operation | Example 1 Rh/Ligand I (Control) | Example 6 Rh/Os/Ligand I |
|---|---|---|
| | Percent Ligand I Remaining | |
| 1 | 100 | 91 |
| 5 | 72 | 79 |
| 8 | 66 | 69 |
| 12 | 53 | 59 |
| 15 | 49 | — |

The results shown in Tables 8, 9 and 10 above lead to the following conclusions: Under conditions which cause significant Ligand I decomposition in continuous propylene hydroformylation in Examples 1, the extent of Ligand I decomposition is significantly lowered when cobalt, platinum, ruthenium or palladium are used as stabilizers.

The compositions of the hydroformylation reaction mixtures used in Examples 7 and 8 are given above in Table 1. Example 7 was the control (no added stabilizer) and Example 8 employed added cobalt as stabilizer. The average reaction rates for Examples 7 and 8 (in terms of gram moles per liter per hour of the butyraldehyde products) as well as the n-butyraldehyde to iso-butyraldehyde product ratio (N/I) are given in Tables 11 and 12 below.

TABLE 11

Example 7. Ligand II, Control (no stabilizer added)
Reaction Rate Test Results - Daily Averages

| Days of Operation | Partial Pressure (psia) | | | Rate gmol/L/hr | N/I Ratio |
|---|---|---|---|---|---|
| | CO | H2 | C3H6 | | |
| 0.6 | 53.1 | 46.4 | 13.3 | 2.050 | 0.8 |
| 1.5 | 51.3 | 47.4 | 16.5 | 1.732 | 0.7 |

TABLE 12

Example 8. Ligand II, Cobalt stabilizer
Reaction Rate Test Results - Daily Averages

| Days of Operation | Partial Pressures (psia) | | | Rate gmol/L/hr | N/I Ratio |
|---|---|---|---|---|---|
| | CO | H2 | C3H6 | | |
| 0.5 | 47.8 | 47.5 | 11.3 | 0.975 | 1.0 |
| 1.4 | 52.4 | 46.2 | 14.5 | 0.628 | 1.5 |

Analysis of the crude reaction products by Phosphorus-31 Nuclear Magnetic Resonance (P-31 NMR) spectroscopy showed that Ligand II in control Example 7 (no added metal stabilizer) had undergone over 50% decomposition to several phosphorus-containing byproducts whereas the reaction mixture containing the cobalt stabilizer (Example 8) showed no decomposition byproducts in the P-31 NMR spectrum.

EXAMPLES 9 TO 14

Examples 9 and 14 below illustrate the stabilization of rhodium in hydroformylation reaction mixtures containing rhodium/phosphite complex catalysts using various transition metal stabilizers. The crude hydroformylation reaction products produced in the continuous hydroformylation tests described in Examples 1 to 6 above were subjected to a rhodium loss test to determine the effect of the Group VIII metal that had been added to stabilize the phosphite in also stabilizing rhodium against precipitation as insoluble complexes or as metallic rhodium. This rhodium loss test simulates harsh hydroformylation reaction conditions in order to accelerate and magnify the rhodium loss phenomenon and to allow meaningful measurements within a shorter time frame. For this test, each crude reaction product was first analyzed for rhodium by Atomic Absorption Spectroscopy (AA) and was then heated in a Fischer-Porter pressure bottle at 130° C. under 10 psig hydrogen for 20 hours. The resulting solution was filtered through a 0.5 micron filter to remove any insoluble complexes and analyzed by AA to determine the concentration of the remaining soluble rhodium. The rhodium concentration before and after these experiments is given in Table 13.

TABLE 13

Rhodium Loss Test Result Using Rhodium Ligand I Catalyst and Transition Metal Stabilizers.

| Example | Stabilizer | Rh Before Test ppm | Rh After Test ppm | Soluble RH Remaining Percent |
|---|---|---|---|---|
| 9 | None | 229 | 56 | 25 |
| 10 | Ruthenium | 245 | 212 | 87 |

TABLE 13-continued

Rhodium Loss Test Result Using Rhodium Ligand I Catalyst and Transition Metal Stabilizers.

| Example | Stabilizer | Rh Before Test ppm | Rh After Test ppm | Soluble RH Remaining Percent |
|---|---|---|---|---|
| 11 | Platinum | 205 | 143 | 70 |
| 12 | Cobalt | 219 | 102 | 46 |
| 13 | Osmium | 184 | 73 | 40 |
| 14 | Palladium | 195 | 36 | 18 |

The results in Table 13 show that (except for palladium) the metal stabilizes the rhodium.

EXAMPLE 15

The purpose of this Example was to determine whether daily additions of dodecane epoxide to a hydroformylation reaction mixture containing a rhodium/Ligand I complex catalyst stabilizes ring hydroformylation relative to a control containing no epoxide. Dodecane epoxide is disclosed in above-mentioned published European patent Application 0590611 as a stabilizer to reduce the acid-catalyzed hydrolytic degradation of phosphites. A rhodium/ruthenium/Ligand I complex catalyst was also tested simultaneously to compare its performance under identical hydroformylation conditions.

In this Example, three glass pressure reactors were used as described in Example 1 above. The composition of the reaction mixture for the epoxide-addition experiment and the control experiment (no epoxide and no metal stabilizer) is shown in Table 1 (see Example 1 in Table 1). The composition of the reaction mixture for the experiment involving the rhodium/ruthenium/Ligand I catalyst is shown in Table 1 (see Example 2 in Table 1). The experimental conditions and reaction rate data from the three tests are shown in Tables 14 to 17 below.

TABLE 14

Control. Rh/Ligand I Catalyst
Reaction Rate Test Results - Daily Averages

| Days Operation | Partial Pressures, psi | | | Rate gmol/L/hr | N/I |
|---|---|---|---|---|---|
| | CO | H2 | C3H6 | | |
| 0.8 | 41.7 | 41.2 | 19.1 | 0.936 | 0.7 |
| 1.5 | 41.6 | 40.6 | 7.7 | 1.086 | 0.7 |
| 2.5 | 43.1 | 41.6 | 3.8 | 1.844 | 0.8 |
| 3.4 | 44.8 | 43.0 | 3.3 | 0.966 | 0.8 |
| 4.5 | 45.4 | 43.4 | 2.4 | 1.530 | 0.9 |
| 5.4 | 45.5 | 43.4 | 2.6 | 1.514 | 0.8 |
| 6.5 | 45.5 | 44.2 | 2.5 | 1.544 | 0.9 |
| 7.5 | 45.3 | 43.8 | 2.6 | 1.531 | 0.9 |
| 8.5 | 45.8 | 44.1 | 2.7 | 1.583 | 0.9 |
| 9.5 | 45.0 | 43.6 | 3.2 | 1.705 | 0.9 |
| 10.5 | 45.6 | 44.2 | 2.8 | 1.687 | 0.9 |
| 11.1 | 45.7 | 44.5 | 2.9 | 1.879 | 2.3 |
| 12.2 | 45.8 | 44.1 | 3.1 | 1.557 | 0.9 |

TABLE 15

Epoxide added daily to a Rh/Ligand I Catalyst
Reaction Rate Test Results - Daily Averages

| Days | Partial Pressures, psi | | | Rate | |
| Operation | CO | H2 | C3H6 | gmol/L/hr | N/I |
|---|---|---|---|---|---|
| Target | 45.0 | 45.0 | 10.0 | 2.000 | 0.0 |
| 0.5 | 43.3 | 40.3 | 28.7 | 1.652 | 0.7 |
| 1.5 | 38.9 | 37.5 | 16.0 | 2.127 | 0.7 |
| 2.5 | 40.2 | 37.9 | 15.9 | 2.135 | 0.7 |
| 3.5 | 40.9 | 37.9 | 15.8 | 2.122 | 0.7 |
| 4.5 | 41.2 | 39.1 | 14.6 | 2.089 | 0.7 |
| 5.5 | 40.8 | 38.9 | 15.8 | 2.072 | 0.7 |
| 6.4 | 41.0 | 38.7 | 16.3 | 3.912 | 0.7 |
| 7.5 | 41.0 | 38.6 | 17.1 | 1.991 | 0.7 |
| 8.5 | 41.8 | 40.3 | 16.4 | 2.023 | 0.7 |
| 9.5 | 41.7 | 40.2 | 17.5 | 2.024 | 0.7 |
| 10.4 | 42.5 | 41.5 | 16.5 | 1.856 | 0.8 |
| 11.5 | 42.4 | 41.0 | 17.8 | 1.971 | 0.7 |

TABLE 16

Ruthenium Stabilizer Comparison
Reaction Rate Test Results - Daily Averages

| Days | Partial Pressures, psi | | | Rate | |
| Operation | CO | H2 | C3H6 | gmol/L/hr | N/I |
|---|---|---|---|---|---|
| Target | 45.0 | 45.0 | 10.0 | 2.000 | 0.0 |
| 0.6 | 49.0 | 45.4 | 32.7 | 0.532 | 1.0 |
| 1.5 | 48.7 | 46.4 | 30.2 | 0.701 | 0.9 |
| 2.5 | 47.2 | 45.6 | 31.3 | 0.862 | 0.9 |
| 3.5 | 46.8 | 45.0 | 31.1 | 1.017 | 0.8 |
| 4.5 | 46.3 | 44.7 | 30.9 | 1.195 | 0.8 |
| 5.6 | 45.8 | 44.4 | 30.6 | 1.383 | 0.8 |
| 6.5 | 46.1 | 44.5 | 29.3 | 1.468 | 0.8 |
| 7.5 | 45.1 | 43.3 | 31.9 | 1.477 | 0.8 |
| 8.5 | 45.4 | 44.1 | 30.5 | 1.306 | 0.8 |
| 9.5 | 46.1 | 44.1 | 28.7 | 1.354 | 0.8 |
| 10.4 | 45.9 | 44.4 | 28.6 | 2.525 | 0.8 |
| 11.4 | 45.0 | 43.7 | 30.9 | 1.426 | 0.8 |

After about twelve days of continuous operation, crude hydroformylation reaction products were withdrawn from each reactor and analyzed by phosphorus-31 Nuclear Magnetic Resonance (NMR) spectroscopy. Analysis of the NMR result shows that ligand decomposition occurred in all three hydroformylation reactions but the decomposition was lowest in the hydroformylation reaction with ruthenium as stabilizer and highest in the hydroformylation reaction to which 0.2 ml dodecane epoxide was added. These results are shown in Table 17.

TABLE 17

Ligand I Stability
Epoxide vs Ruthenium Comparison

Ligand Stabilities as Determined by
Relative Areas of P-31 NMR Peaks

| | Ligand Remaining Peak Counts | Ligand Decomposition Products Peak Counts | Ligand Remaining |
|---|---|---|---|
| Control (no additives) | 5724 | 4103 | 58% |
| Epoxide (added daily) | 1874 | 7048 | 21% |
| Ruthenium additive | 4677 | 1608 | 74% |

What is claimed is:

1. A hydroformylation catalyst precursor composition comprising: (i) a rhodium catalyst precursor, (ii) a precursor compound of a Group VIII metal (other than a rhodium compound) in an amount that provides a sufficient amount of the Group VIII metal to reduce the rhodium-catalyzed decomposition of the phosphite described in (iii) below during hydroformylation and (iii) a phosphite in which each phosphorus atom is bonded to three oxygen atoms and at least one such oxygen atom is bonded to a carbon atom of an aromatic ring that is adjacent to another carbon atom of said ring having a pendant monovalent group having a steric hindrance at least as great as the steric hindrance of the isopropyl group.

2. A hydroformylation catalyst composition comprising: (i) rhodium in complex combination with carbon monoxide and a phosphite in which each phosphorus atom is bonded to three oxygen atoms and at least one such oxygen atom is bonded to a carbon atom of an aromatic ring that is adjacent to another carbon atom of said ring having a pendant monovalent group having a steric hindrance at least as great as the steric hindrance of the isopropyl group, and (ii) a Group VIII metal (other than a rhodium compound) in complex combination with carbon monoxide and said phosphite, said Group VIII metal being present in an amount sufficient to reduce rhodium-catalyzed decomposition of the phosphite during hydroformylation.

* * * * *